(12) United States Patent
Wang et al.

(10) Patent No.: US 9,962,127 B2
(45) Date of Patent: May 8, 2018

(54) INTRAVASCULAR OPTICAL IMAGING SYSTEM

(71) Applicant: Erasmus University Medical Center Rotterdam, Rotterdam (NL)

(72) Inventors: Tianshi Wang, Rotterdam (NL); Charles Theodoor Lancee, Hoogersmilde (NL); Antonius Franciscus Wilhelmus Van Der Steen, Rotterdam (NL); Gijs Van Soest, Moordrecht (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 37 days.

(21) Appl. No.: 14/778,380

(22) PCT Filed: Mar. 17, 2014

(86) PCT No.: PCT/EP2014/055342
§ 371 (c)(1),
(2) Date: Sep. 18, 2015

(87) PCT Pub. No.: WO2014/147039
PCT Pub. Date: Sep. 25, 2014

(65) Prior Publication Data
US 2016/0228071 A1    Aug. 11, 2016

(30) Foreign Application Priority Data
Mar. 19, 2013  (GB) .................................. 1305031.5

(51) Int. Cl.
*A61B 5/02*  (2006.01)
*A61B 5/00*  (2006.01)
(Continued)

(52) U.S. Cl.
CPC .......... *A61B 5/7285* (2013.01); *A61B 5/0066* (2013.01); *A61B 5/0084* (2013.01);
(Continued)

(58) Field of Classification Search
CPC ... A61B 5/7285; A61B 5/0084; A61B 5/0205; A61B 5/7282; A61B 5/6852
See application file for complete search history.

(56) References Cited

U.S. PATENT DOCUMENTS 5,321,501 A   6/1994  Swanson et al.
5,375,602 A   12/1994 Lancee et al.
(Continued)

FOREIGN PATENT DOCUMENTS

WO   WO 2011/038048 A1   3/2011

OTHER PUBLICATIONS

Ha, Jinyong et al. "Compensation of motion artifacts in intracoronary optical frequency domain imaging and optical coherence tomography" Int. J. Cardiovascular Imaging (2012) 28:1299-1304.
(Continued)

*Primary Examiner* — Robert N Wieland
(74) *Attorney, Agent, or Firm* — Wolf, Greenfield & Sacks, P.C.

(57) ABSTRACT

A catheter-based optical imaging system for imaging a patient includes a catheter-based imaging device configured to direct optical radiation towards a vessel wall and to receive reflected radiation therefrom. A displacement mechanism is configured to vary the position of the imaging device relative to the catheter as a function of time during an imaging scan. An input is configured to receive cardiac event timing data, such as ECG data, from the patient. A trigger module is configured to initiate an imaging scan based on the cardiac event timing obtained from the cardiac event timing (Continued)

data. By triggering the optical imaging scans between cardiac events, artifacts in the image data can be reduced or eliminated.

24 Claims, 10 Drawing Sheets

(51) Int. Cl.
  *A61B 5/0452* (2006.01)
  *A61B 5/0205* (2006.01)
  *A61B 5/044* (2006.01)
  *A61B 7/00* (2006.01)

(52) U.S. Cl.
  CPC ........ *A61B 5/0205* (2013.01); *A61B 5/02007* (2013.01); *A61B 5/044* (2013.01); *A61B 5/0452* (2013.01); *A61B 5/6852* (2013.01); *A61B 5/7282* (2013.01); *A61B 7/00* (2013.01)

(56) References Cited

U.S. PATENT DOCUMENTS

| | | | |
|---|---|---|---|
| 5,740,808 A | 4/1998 | Panescu et al. | |
| 8,285,368 B2 | 10/2012 | Chen et al. | |
| 2002/0049375 A1 | 4/2002 | Strommer et al. | |
| 2007/0167833 A1 | 7/2007 | Redel et al. | |
| 2008/0146918 A1* | 6/2008 | Magnin | A61B 8/54 600/437 |
| 2008/0146942 A1* | 6/2008 | Dala-Krishna | A61B 6/12 600/466 |
| 2010/0105980 A1 | 4/2010 | Shimizu et al. | |
| 2012/0197113 A1* | 8/2012 | Courtney | A61B 8/12 600/427 |
| 2012/0212595 A1* | 8/2012 | Parmar | A61B 5/0062 348/68 |
| 2013/0216114 A1* | 8/2013 | Courtney | A61B 5/0066 382/130 |

OTHER PUBLICATIONS

Great Britain Search Report from Application No. GB1305031.5 dated Aug. 22, 2013.
International Search Report and Written opinion dated Sep. 9, 2014 from corresponding International Application No. PCT/EP2014/055342.

* cited by examiner

INTRAVASCULAR OPTICAL IMAGING SYSTEM

This application is the national phase of International Application No. PCT/EP2014/055342, filed on Mar. 17, 2014, which claims the priority benefit of Great Britain Application No. 1305031.5, filed on Mar. 19, 2013, which applications are hereby incorporated by reference to the maximum extent allowable by law.

The present invention relates to optical imaging systems for imaging internal structures of the human or animal body. In particular, though not exclusively, the invention relates to imaging systems which can be used for intracoronary imaging.

Cardiovascular diseases are responsible for 30% of all deaths worldwide. Nearly half of cardiac deaths are due to acute coronary syndromes, while most of those are triggered by rupture of a vulnerable atherosclerotic plaque. In 2001, optical coherence tomography (OCT) was first applied in intracoronary imaging in humans and showed promising capability as a powerful tool for diagnostic imaging for arterial wall pathologies and for guidance of coronary interventions such as stent.

In endoscopic OCT for coronary imaging, established methods use a guide wire to direct a catheter along a lumen of an artery. With reference to FIG. 1, an imaging light beam 1 emitted from a distal end 2 of a catheter 3 scans the wall 4 of the artery 5. The catheter 3 rotates about its own axis (as indicated by arrow 6) to continuously sweep the imaging light beam 1 in a rotary fashion through successive radial directions, and collects the back-reflected light, which carries information relating to the illuminated tissue. A coherence fringe signal of the back-reflected light is obtained by combining it with a reference light beam. The fringe signal is converted into an electronic signal, digitized, and stored. The coherence fringe signal data corresponding to each wavelength sweep of the laser, such as 1210-1310 nm, is further processed by inverse Fourier transform. The data corresponding to each wavelength sweep after inverse Fourier transform forms an A-line. The rotational movement 6 of the catheter 3 enables A-lines to be generated for multiple radial directions each corresponding to a circumferential position on the artery thereby generating a 2D image of a cross section of the artery. Each 2D image of an artery cross section may be formed by approximately 500 lines or more, corresponding to a full circumferential (360°) scan by the catheter 3. This full circumferential scan may be referred to herein as a "frame". 3D imaging of the artery 5 may be achieved by longitudinal translational motion (as indicated by arrow 7) of the catheter 3 along the artery 5 (also referred to herein as "pulling back" the catheter) while the catheter is rotating. The catheter scan will thereby sweep out a helical path of successive A-lines to form the full 3D dataset. Each 360 degree rotation within the helical path may also be referred to as a frame, and multiple frames are generated along the longitudinal (z) axis.

A problem which has been found to arise in coronary imaging is that of motion artefact in which the images generated are sub-optimal caused by movement of the artery during scanning. It is an object of the present invention to avoid or at least mitigate problems arising from motion artefact and thereby improve image quality.

According to one aspect, the present invention provides a catheter-based optical imaging system for imaging a patient, comprising:

a catheter-based imaging device configured to direct optical radiation towards a vessel wall and to receive reflected radiation therefrom;
a displacement mechanism configured to vary the position of the imaging device relative to the catheter as a function of time during an imaging scan;
an input configured to receive cardiac event timing data from the patient; and
a trigger module configured to initiate an imaging scan based on the cardiac event timing data.

The input module may be configured to receive physiological signals from the patient, from which physiological signals the cardiac event timing data is obtained. The cardiac event timing data may be obtained from any one or more of: ECG data; blood pressure measurement data; blood oxygen measurement data; phonocardiogram data; and visual echocardiogram data. The imaging system may include one or more of: an ECG sensor; a blood pressure sensor, an SpO2 sensor; a phonocardiogram sensor; and a visual echocardiogram sensor. The trigger module may be configured to effectuate an imaging scan within a period defined between two cardiac events identified within the cardiac event timing data. The trigger module may be configured to effectuate an imaging scan between the end of a cardiac T-wave and the beginning of a successive R-wave. The trigger module may be configured to effectuate an imaging scan between the end of a cardiac T-wave and the beginning of a successive T-wave. The trigger module may be configured to effectuate an imaging scan a predetermined time after detection of a selected cardiac event.

The imaging system may be configured such that:
the imaging device includes an optical element rotatable about the catheter longitudinal axis to generate frames of image data, each frame corresponding to at least part of a circumferential scan, and
the displacement mechanism comprises a longitudinal displacement mechanism configured to drive the optical element along a longitudinal axis of the catheter such that successive frames of image data correspond to different longitudinal positions, and
the trigger module is configured to initiate longitudinal displacement of the optical element by the displacement mechanism by reference to a detected cardiac event.

The trigger module may be further configured to initiate rotation of the optical element by reference to a detected cardiac event and to initiate said longitudinal displacement of the optical element in a period after initiating rotation, when the optical element has reached a predetermined speed of rotation. The detected cardiac event may be one of a QRS complex or a T-wave. The optical element may comprise a first transmissive interface, a second transmissive interface and a first reflective surface and the imaging system may include a motor coupled to rotate the optical element. The first transmissive interface may be positioned and configured to optically couple the optical element to an optical channel disposed along the catheter and the second transmissive interface may be positioned and configured to direct optical radiation along optical paths extending radially from the catheter longitudinal axis, the first reflective surface being disposed between the first and second transmissive interfaces. One or more of the first transmissive interface, the second transmissive interface and the first reflective surface may comprise a focusing element.

The imaging system may further include an inner catheter slidably disposed within an outer catheter, in which the catheter-based imaging device is mounted to a distal end of the inner catheter, and the displacement mechanism may further comprise: a motor-driven moveable part to which the proximal end of the inner catheter is attached; and a fixed part to which the proximal end of the outer catheter is attached.

The catheter-based imaging device may be mounted to a distal end of an inner catheter, the inner catheter further comprising: an optical conduit extending through the inner catheter from the proximal end to a position adjacent the imaging device for optical coupling thereto; motor control cables extending through the inner catheter from the proximal end to a motor at the distal end of the inner catheter; and a connector coupled to the proximal end of the inner catheter configured to communicate both optical conduit and motor control cables into the catheter.

According to another aspect, the present invention provides a method of optical imaging within a vessel of a patient, comprising the steps of:
 introducing a catheter-based imaging device into a vessel of a patient, the imaging device configured to direct optical radiation towards the vessel wall and to receive reflected radiation therefrom;
 obtaining cardiac event timing data from the patient;
 initiating an imaging scan based on the cardiac event timing; and
 using a displacement mechanism to vary the position of the imaging device relative to the catheter as a function of time during the imaging scan.

The cardiac event timing data may be derived from measured physiological signals from the patient. The cardiac event timing data may be obtained from any one or more of: ECG data; blood pressure measurement data; blood oxygen measurement data; phonocardiogram data; and visual echocardiogram data.

According to another aspect, the present invention provides a catheter-based optical imaging system for imaging a patient, comprising:
 an optical pathway extending along a catheter in an axial direction from a proximal end to a distal end;
 an optical element disposed at the distal end of the catheter configured to direct optical radiation from the axial optical path to a radial optical path extending radially from the catheter longitudinal axis towards a vessel wall and to receive reflected radiation therefrom; wherein:
 the optical element is rotatable about the catheter longitudinal axis so as to vary the direction of the radial optical path; and
 the optical element comprises a first transmissive interface, a second transmissive interface and a first reflective interface.

The first transmissive interface may be positioned and configured to optically couple the optical element to the optical pathway extending along the catheter and the second transmissive interface may be positioned and configured to direct optical radiation along the radial optical path, the first reflective surface being disposed between the first and second transmissive interfaces. One or more of the first transmissive interface, the second transmissive interface and the first reflective surface may comprise a focusing element. The, or each, focusing element may comprise a concave or convex surface or interface. The, or each, focussing element may comprise a spherical surface.

Embodiments of the present invention will now be described by way of example and with reference to the accompanying drawings in which.

Figure 1:
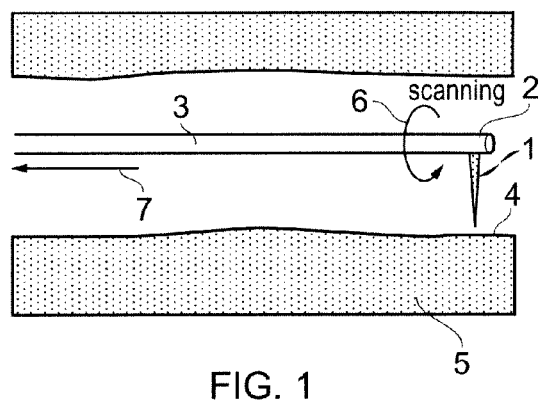
FIG. 1 is a schematic side view of a probe for endoscopic optical coherence tomography in coronary imaging.
Figure 2:
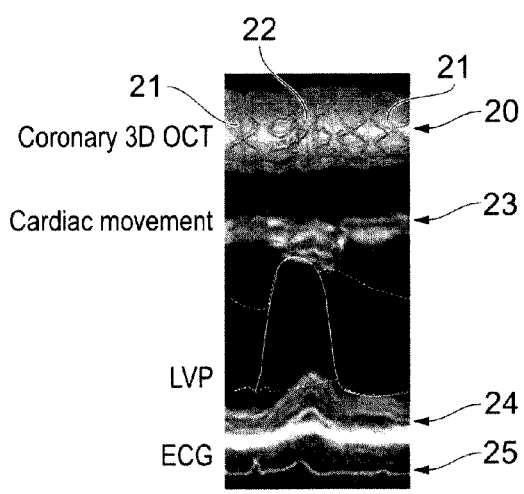
FIG. 2 is a collection of aligned images showing: an OCT image of a longitudinal section of coronary artery; a representation of cardiac movement during the time period for generating the OCT image; a plot of left ventricular blood pressure during the same period; and a plot of ECG data during the same period.

At least one aspect of motion artefact is caused by the strong movement of the heart during the systolic phase of the heart cycle. This phase can be recognized in the electrocardiogram (ECG) by the R-peak and subsequent S- and T-waves. The cardiac motion during acquisition will cause inaccuracy in frame spacing and possibly frame order, due to motion of the catheter along the vessel. This can compromise the fidelity of the longitudinal rendering and the 3D visualization of the data. The deformation in the longitudinal image (along the artery) of a pullback data set due to cardiac motion is shown in FIG. 2. FIG. 2 shows at 20 an image of a longitudinal section of coronary artery which includes a stent. The stent has a regular trellis-like framework of intersecting elements 21 which it can readily be seen have been rendered in the image in a somewhat irregular pattern which is particularly disrupted in a central location 22 which coincides with a large disturbance caused by cardiac movement, represented in image 23, and with left ventricular blood pressure represented at image 24 and with electrocardiogram wave data represented at image 25.

Figure 3A:
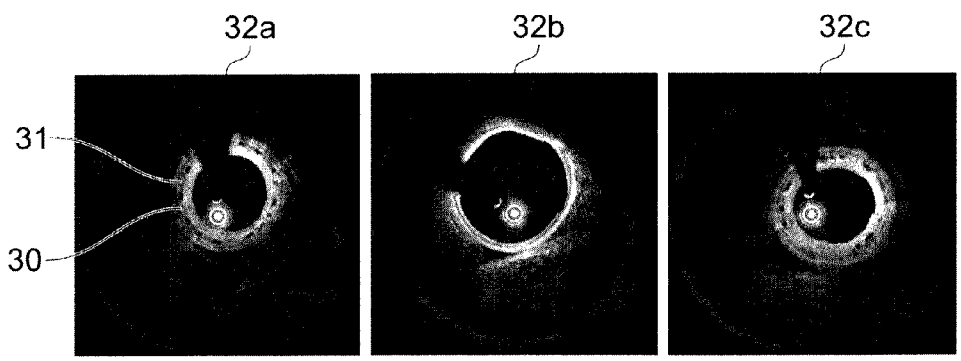
FIGS. 3a and 3b are sequential sets of cross-sectional images from the 2D OCT scan data.
Figure 3B:
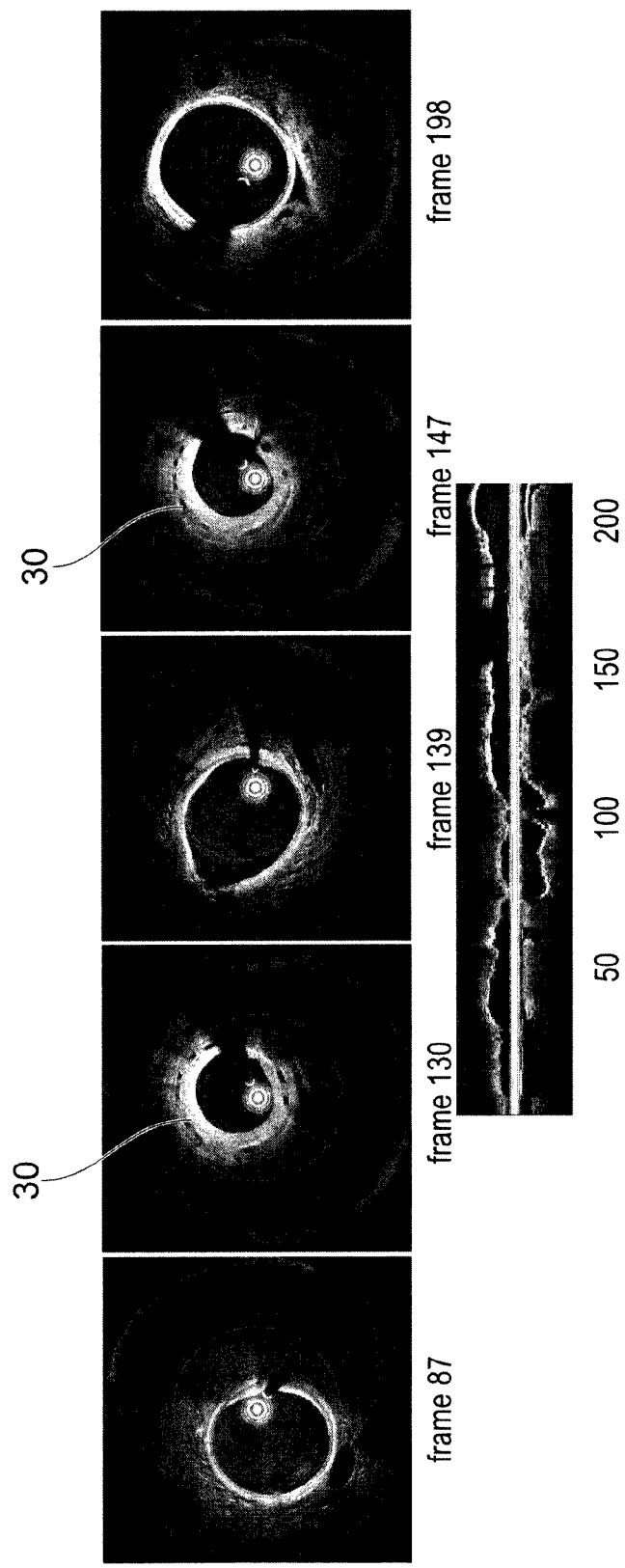

Reversal of frame order due to cardiac motion is shown in FIGS. 3a and 3b. FIG. 3a shows a series of three frames which provide three cross sections of the artery chronologically sequenced from a longitudinal scan (pullback) of the catheter. An edge of a stent 30 (apparent by the periodic structure 31) shows up in a first frame 32a, disappears in a second frame 32b and then reappears in the third frame 32c. In effect, cardiac motion causes the tissue wall to "overtake" the longitudinal motion of the catheter during pullback and the edge of the stent appears more than once in successive 2D images recorded during pullback. A more complete sequence is shown in FIG. 3b showing five images which provide five cross sections of the artery chronologically sequenced by frame numbers 87, 130, 139, 147 and 198, from a longitudinal scan (pullback) of the catheter. A 2D representation of the longitudinal sequence is shown below for the full set of frames. The single stent 30 appears twice (frame 130 and frame 147) in a pullback record of 210 frames. The first appearance is in frames 112 to 137 (exemplified at frame 130). The second appearance is in frames 143 to 196 (exemplified at frame 147). The five images show the cross sections of the artery and the frames 87, 139 and 198 show no stent appearing while frames 130, 147 show the stent appearing. Cardiac motion causes the tissue wall to temporarily "overtake" the longitudinal motion of the catheter during pullback and the edge of the stent appears more than once in successive 2D images recorded during pullback. Normally, a pullback length may be 50-100 mm and the speed of pullback may be 20 mm/second. The motion artefact will show up more than once in such a pullback because the duration of a heart cycle is around 1 second in patients undergoing percutaneous coronary intervention (PCI).

To avoid this adverse artifact, one solution is to increase the pullback speed of the catheter 3 so that the pullback procedure can be finished within one heart cycle. However, keeping the imaging speed (e.g. the frame rate) unchanged and simply increasing the pullback speed will aggravate the under-sampling along the artery as shown in FIG. 4.

Figure 4:
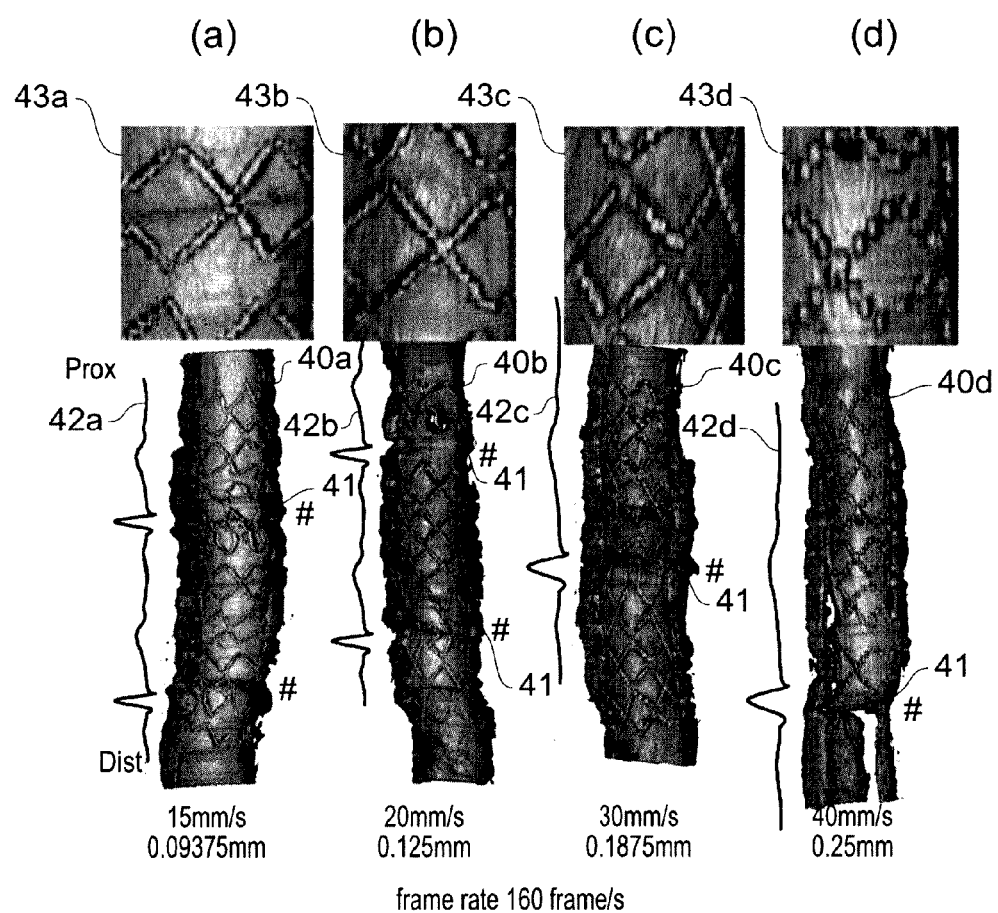
FIG. 4 is a set of four OCT images of a longitudinal section of coronary artery illustrating cardiac motion artefacts.

In FIG. 4, a selection of OCT images is shown obtained under various pull-back speeds. Each image shows a view of a longitudinal segment of the artery in which lies a coronary stent having the visible trellis-like lattice structure. A close-up portion of each image is shown above it. FIG. 4a shows a longitudinal segment 40a acquired using a pullback speed of 15 mm/sec (providing a longitudinal sampling interval of 0.9375 mm from 160 frames per second scan rate); FIG. 4b shows a longitudinal segment 40b acquired using a pullback speed of 20 mm/sec (providing a longitudinal sampling interval of 0.125 mm from 160 frames per second scan rate); FIG. 4c shows a longitudinal segment 40c acquired using a pullback speed of 30 mm/sec (providing a longitudinal sampling interval of 0.1875 mm from 160 frames per second scan rate); and FIG. 4d shows a longitudinal segment 40d acquired using a pullback speed of 40 mm/sec (providing a longitudinal sampling interval of 0.25 mm from 160 frames per second scan rate).

Alongside each scan 40a, 40b, 40c, 40d is shown a corresponding ECG trace 42a, 42b, 42c, 42d which is aligned in time with the data acquisition time along the longitudinal (z) axis of the scan. It can be seen that each ECG pulse correlates closely with a motion artefact 41 indicated by the symbol #. The inset close-up images 43a, 43b, 43c, 43d also show the increasing levels of pixellation in the images caused by the increased speed of pullback.

A further aspect of conducting artery imaging is that the blood is preferably flushed out of the artery with flush medium during imaging. In current clinical applications, the flush medium may be saline or x-ray contrast dye (e.g. Visipaque from GE Healthcare). These iodine-containing fluids are nephrotoxic and hence their use should be limited to a minimum. With a shorter imaging procedure, the flush volume can be further reduced.

Figure 5:
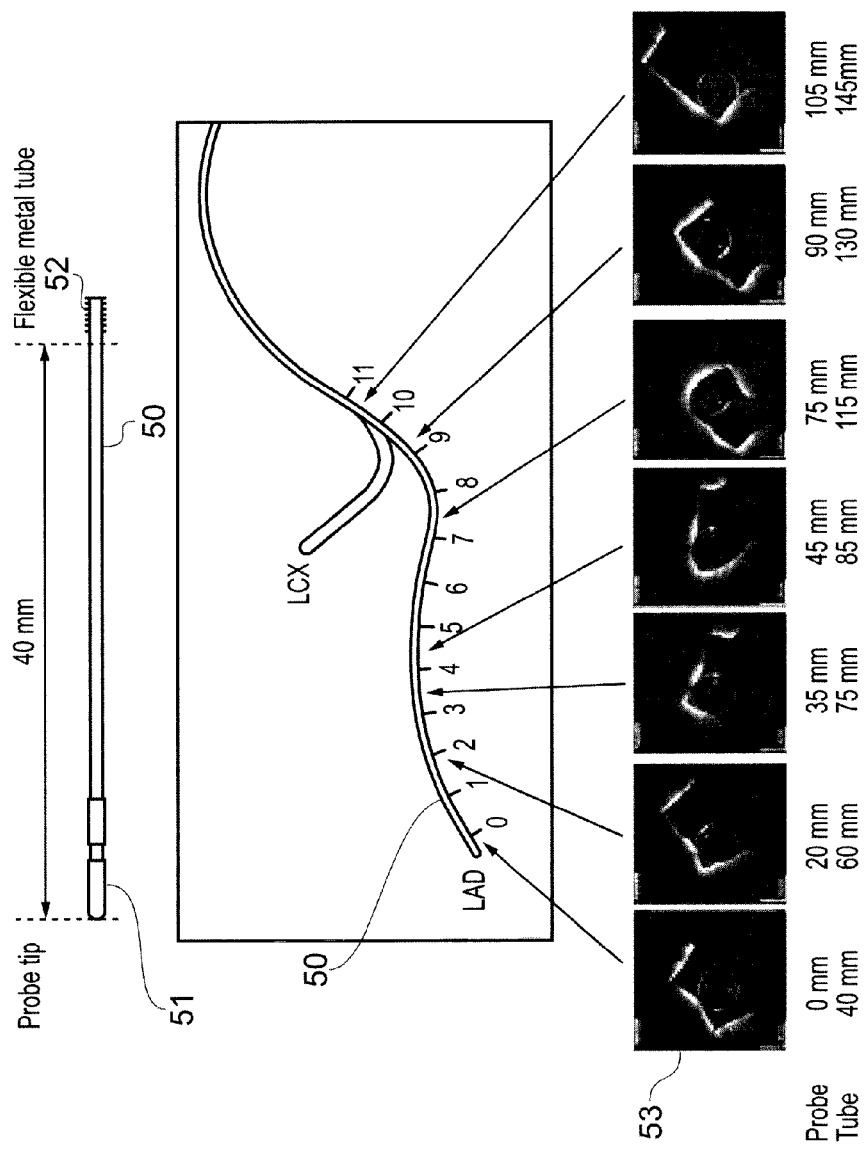
FIG. 5 is a schematic diagram of an OCT probe and images generated thereby illustrating non-uniform rotation distortion.

A further aspect of conducting artery imaging is that of non-uniform rotation distortion. A conventional method to drive an OCT catheter is to rotate the inner components of the catheter by a proximal motor, i.e. a motor disposed towards a proximal end of the catheter 3 remote from the distal end 2 and the imaging tip. Because of the variable mechanical resistance along the curved catheter, the rotation speed of the distal tip may not be constant, leading to non-uniform rotation distortion (NURD). As seen in FIG. 5, the catheter 50 has a probe tip 51 providing the imaging tip extending 40 mm out of a flexible metal tube 52. Each of the images 53 represents a cross-sectional image taken at a specified longitudinal distance along a square section phantom having varying curvature along its longitudinal extent. It can be seen that each section has varying degrees of distortion caused by non-uniform rotation caused by varying degrees of curvature of the vessel.

One option for reducing or eliminating this effect is to provide rotation of the imaging tip by a local micro-motor at the distal end of the catheter powered by electrical leads extending the length of the catheter, as will be described in more detail later.

Figure 6:
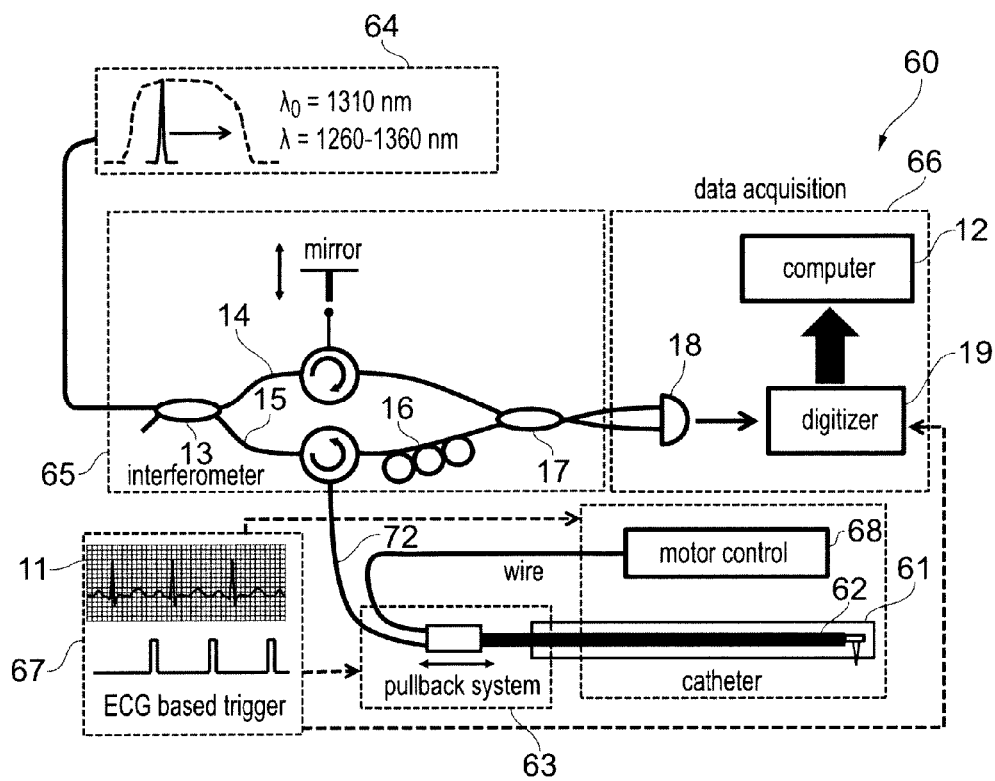
FIG. 6 is a schematic diagram of a high-speed optical imaging system with ECG-based triggering.

FIG. 6 shows a schematic diagram of a high-speed optical imaging system which is configured to complete imaging of an entire artery within one cardiac cycle while maintaining a small sampling pitch along the artery. By means of the high-speed optical imaging system, cardiac motion artefact can be eliminated and the amount of flush medium can be significantly reduced. The uniformity of rotation of the probe tip can also be increased.

With reference to FIG. 6, the high-speed intravascular optical imaging system 60 for coronary imaging comprises an outer catheter 61 or transparent tube; an inner catheter 62 supporting an imaging device; a pullback system 63 coupled to the inner catheter 62 for providing longitudinal (z-direction) displacement of the imaging device; a high-speed frequency-scanning laser 64; an interferometer 65; a data acquisition system 66; and an electrocardiography trigger module 67. Also provided may be a display 11, control hardware and data storage such as computer 12. The pullback system may include a motor controller 68. The interferometer 65 includes optical paths comprising: a 2×2 coupler 13, a reference arm 14, a sample measurement arm 15 with polarization controller 16, and a 2×2 coupler 17 providing an output path from the reference and sample arms to a balanced photonics detector 18 and a digitizer 19.

The operation of the interferometer may be according to known principles and need not be described further in great detail.

In order to complete imaging of an artery within one cardiac cycle, a pullback speed of the imaging device effected by the pullback system 63 should be the length of the artery or artery segment for imaging divided by the duration of one cardiac cycle.

The cardiac cycle of a healthy adult is typically 0.6-1.0 second. Patients undergoing percutaneous coronary intervention may be given medication to slow the heart cycle to approximately 60 beats per minute, i.e. each cardiac cycle lasts 1 second in duration. The time period suitable for imaging is the time between the T-wave in the ECG and the R-wave in the next cardiac cycle. This period represents approximately 60-70% of the cardiac cycle.

The relevant length of an artery for imaging, required for diagnostics and stent positioning, is typically 60-80 mm although it may be longer, particularly in the right coronary artery. Imaging a length of artery of 70 mm in 0.7 sec requires pullback speed of 100 mm/sec. Typical commercial OCT systems use a frame pitch (longitudinal sampling interval) of maximally 250 µm. A high-speed pullback at this pitch requires a frame rate of 400 frames/sec, meaning that the imaging device must be rotated at 400 revolutions per second (rps). To obtain a sampling rate of 500 lines per frame, the swept scanning rate of the laser must be greater than 200 kHz.

A limitation of current intravascular OCT scanners is the limited longitudinal sampling. The width of the focus created by catheter optics is about 30 µm, which is much smaller than the frame pitch. The system described in this specification can perform imaging of the relevant length of coronary artery (e.g. 60-80 mm) in less than one heart cycle with adequate longitudinal sampling. With a frame pitch of 30 µm and 100 mm/s pullback speed, a frame rate of 3.3 kHz is required, and a laser sweep rate of 1.65 MHz. To ensure dense sampling in the transverse direction, 1000 lines per frame are preferable. This can be achieved by a laser that sweeps at 3.3 MHz.

Investigation of larger sections of artery or reduction of the sampling interval leads to proportional increases in pullback speed, frame rate, and laser sweep rate.

Figure 7:
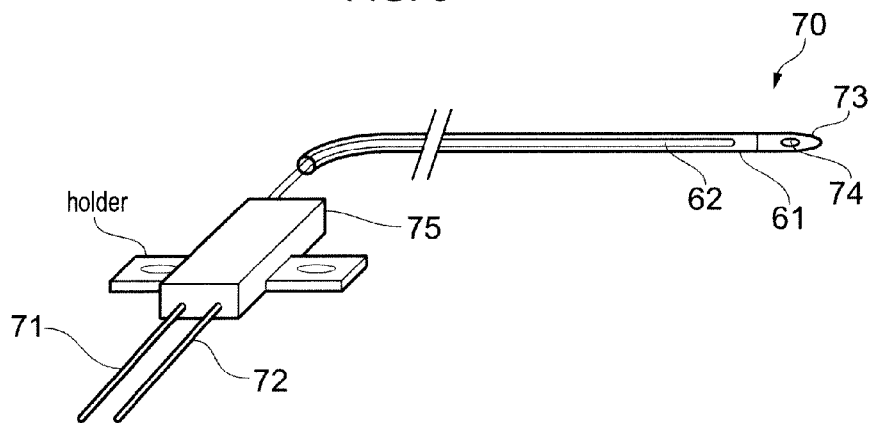
FIG. 7 is a schematic view of an imaging probe and connector used in the optical imaging system of FIG. 6.

In FIG. 7, a preferred arrangement of imaging probe 70 is shown. The imaging probe 70 includes the outer catheter 61 which is a transparent tube suitable for the optical radiation from the laser 64 to pass through and a connector 75 and the inner catheter 62 which supports or contains the imaging device. The inner catheter 62 is coupled to the connector 75 providing as output the control wires 71 for connection to the motor control unit 68 and the optical fibre 72 forming part of the interferometer 65. The outer catheter 61 may include a distal tip 73 which includes a hole 74 for connecting to a guild wire or guide wire (not shown). Such a guide wire may be used to insert the outer catheter 61 into the artery. The imaging probe 70 is inserted into an artery to perform the scanning and the outer catheter 61 remains stationary within the artery while the imaging device supported in or on the inner catheter scans both rotationally about the inner catheter axis and longitudinally under the control of the pullback system to be further described later.

Figure 8:
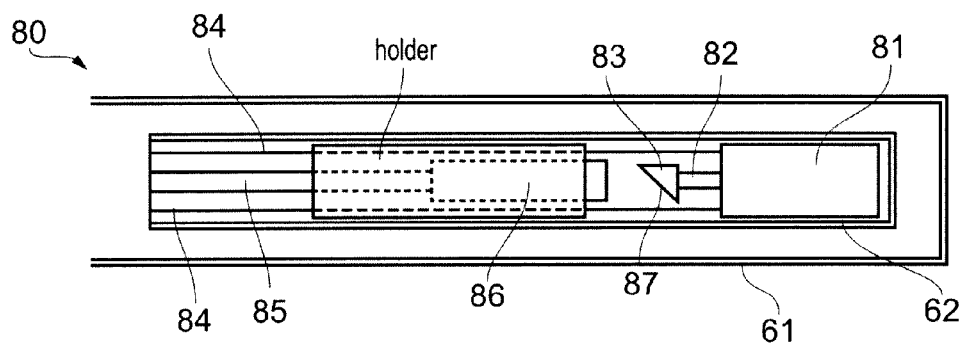
FIG. 8 is a more detailed schematic cross-sectional side view of an imaging probe used in the optical imaging system of FIG. 6.

FIG. 8 shows a schematic diagram of detail of an exemplary imaging probe 80. The outer catheter 61 and inner catheter 62 are provided as tubes which are transparent at least to the wavelengths of optical radiation provided by the frequency-scanning laser 64, at least in the regions of the catheters where the optical radiation has to pass through the walls of the catheters. The distal end of the inner catheter or tube 62 houses a motor 81 having a motor output shaft 82 to which is mounted an optical element 83. Control wires 84 extend along the inner catheter from the proximal end to the motor 81 at the distal end, to provide power supply and control to the motor 81. The control wires 84 may be affixed to or embedded in the walls of the inner catheter 62. An optical fibre 85 extends along the inner catheter 62 from the proximal end to near the distal end at a position terminating at, or just short of, the optical element 83. The end of the optical fibre 85 may include a lens element 86 such as a ball lens or a gradient refractive index lens integrally formed with the fibre. In a simple form, the optical element 83 provides a reflective surface 87 configured to reflect light emerging from the fibre 85/lens 86 along the axis of the fibre to an orthogonal (radial) direction where it passes through the inner and outer catheter walls to illuminate artery walls. As the motor shaft 82 rotates, the optical element rotates about the longitudinal axis of the catheter causing the optical radiation to scan around the axis of the catheter in a circumferential scan (frame).

Preferably, the motor 81 is a synchronous motor which provides full circumferential scanning. It is also possible to provide oscillation scanning where the optical element 83 is oscillated about the catheter axis so that the optical radiation only describes part of a full circumference in the circumferential scan.

Figure 9:
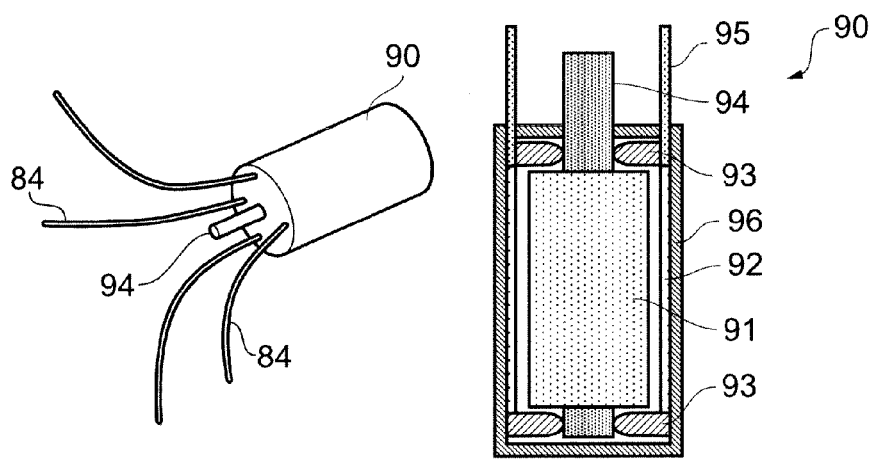
FIG. 9 is a perspective view and cross-sectional schematic view of a synchronous micro-motor suitable for use in the distal end of the imaging probe of FIG. 8.

FIG. 9 shows a schematic cross-sectional diagram of a synchronous micro-motor 90 suitable for implementing the motor 81. The synchronous micro-motor 90 comprises a permanent magnetic rotor 91, coils 92, bearings 93, shaft 94, control/power wires 95 and shield 96. The rotating speed of the synchronous micro-motor 90 is preferably ≥400 revolutions per second. It is driven by a multi-phase sinusoidal current signal via the wires 95. The speed of the motor is synchronized to the frequency of the driving signal. The high rotating speed of the motor can be achieved by increasing the frequency of the driving signal from a lower number or from zero frequency.

Figure 10:
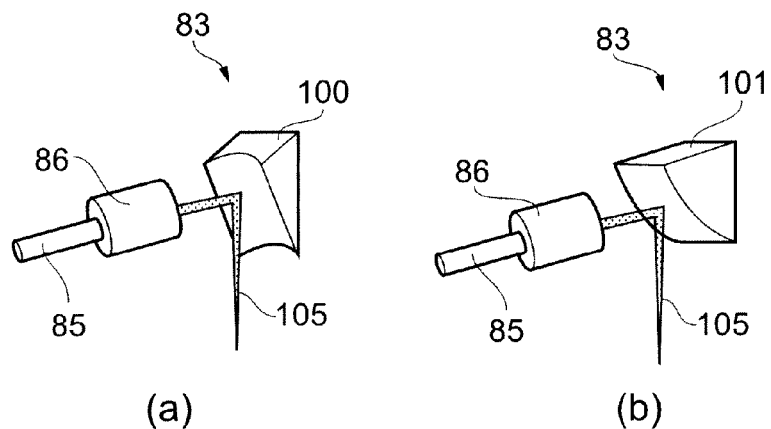
FIG. 10 shows schematic perspective views of two alternative optical elements suitable for use in the imaging probe of FIG. 8.

FIG. 10 shows schematic perspective views of two different exemplary optical elements 83 and their relationship with the optical fibre 85 and lens 86. The optical elements 83 may be used to focus and deflect the light beam emerging from the fibre 85. The fibre 85 may include a GRIN lens or ball lens at the tip of a single mode fibre. The optical element 100 of FIG. 10a combines a reflecting prism or mirror with a concave reflecting surface to provide focusing, further focusing, defocusing, or further defocusing of the radially directed light beam 105, particularly to correct for astigmatism of the light beam. The optical element 101 of FIG. 10b combines a reflecting prism or mirror with a convex reflecting surface to provide focusing or further focusing of the radially directed light beam 105, particularly to correct for astigmatism of the light beam. The transverse resolution of the imaging probe can be improved with such an arrangement. The correction can be made along two optical axes by appropriate selection of concavity or convexity in two orthogonal directions.

Figure 11:
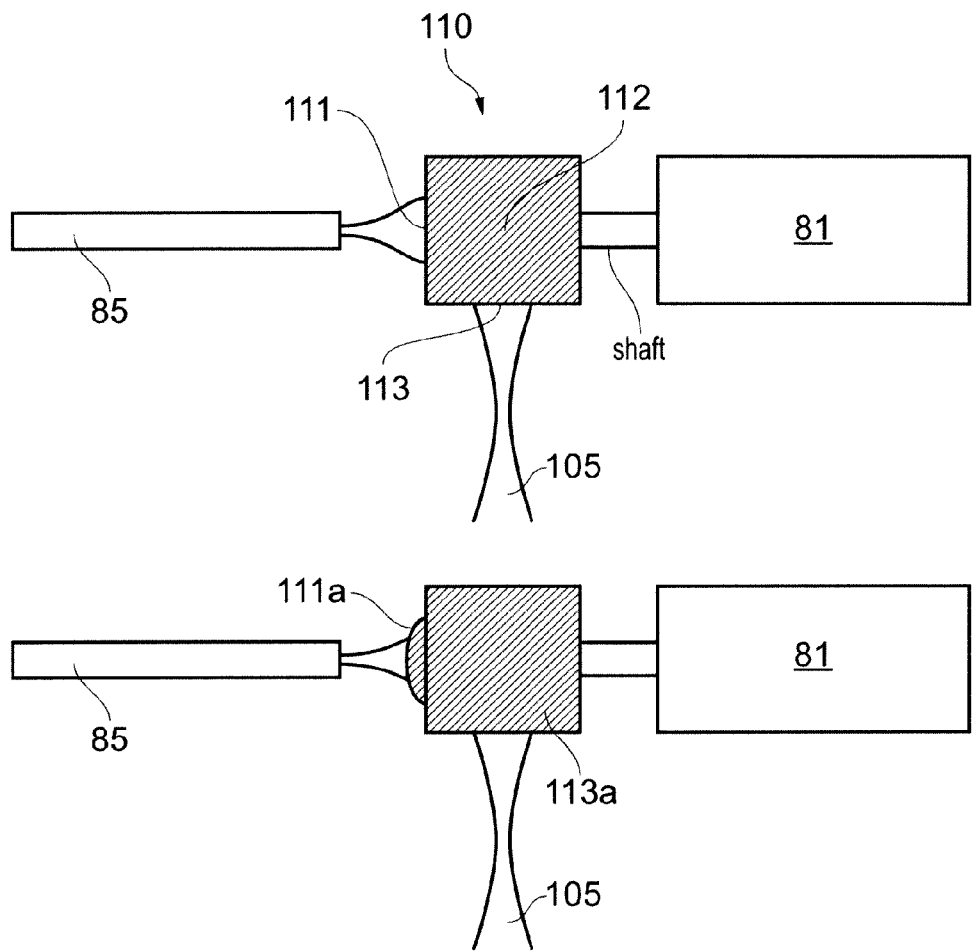
FIG. 11 shows schematic cross-sectional side views of optical elements suitable for use in the imaging probe of FIG. 8.

In a particularly preferred arrangement shown schematically in FIG. 11, the optical element 83 can contain all the required focusing arrangements in one element. A separate lens arrangement at the end of the fibre can then be omitted, reducing the rigid length of the probe, i.e. the portion housing the motor, optics and fibre termination (the length from the emitting surface of the fiber to the distal end of the motor). As shown in FIG. 11, the optical element 110 may comprise three interfaces—a first transmissive interface 111, a reflective surface 112 and a second transmissive interface 113. Reflective surface 112 is used for deflecting the beam. Transmissive interface 111 may include a curved surface (concave or convex—as shown at 111a) for optical coupling to the fibre 85. Transmissive interface 113 may include a curved surface (e.g. convex or concave as shown at 113a) for optimal focusing of the radially directed light beam 105 on the artery walls. Any of the three interfaces/surfaces 111, 112, 113 can be made into a curved surface to perform focusing and/or correction of astigmatism. The curved surfaces may be spherical surfaces for focusing. The optical element 110 is preferably a unitary structure. Providing all of the focusing optics in one element mounted directly to the motor shaft also provides a compact device and simpler, lower cost assembly and design.

Figure 12:
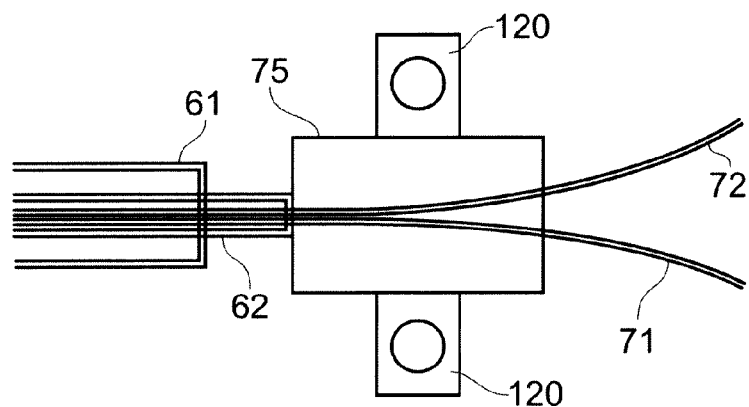
FIG. 12 is a more detailed schematic plan view of the connector and proximal end of the imaging probe of FIG. 7.

As shown in FIG. 12, the connector 75 is used to collect the motor control wires 71 and optical fibre 72 from the proximal end of the inner catheter 62, to which it is connected. This connector 75 has mounting plates 120 for mounting the connector onto a pullback system 63, as shown in more detail in the schematic diagram of FIG. 13. In a general aspect, the connector 75 is configured to communicate both optical conduit and motor control cables into the inner catheter 62. This communication may be by suitable electrical and optical connectors, or it may be by directing the electrical control wires 71 and the optical fibre 72 out of the catheter.

Figure 13:
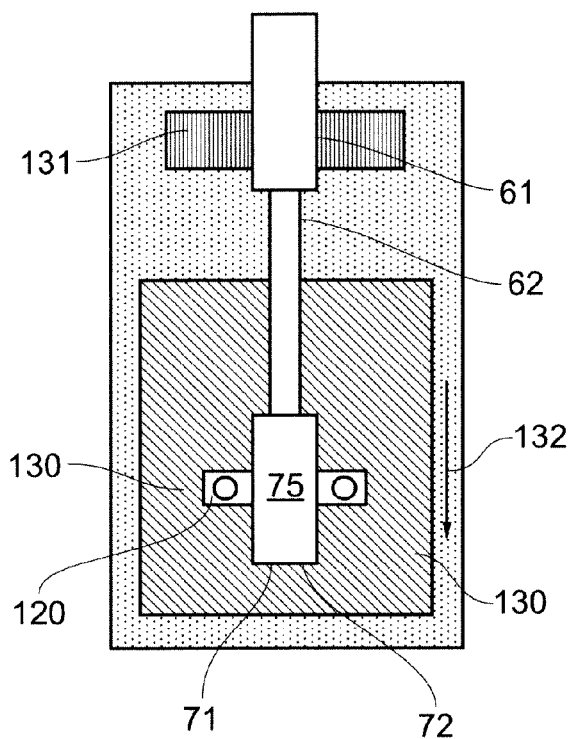
FIG. 13 is a schematic plan view of a pullback system suitable for use in the optical imaging system of FIG. 6.

As shown in FIG. 13, the connector 75 is mounted onto a moveable part such as a transport table 130 while the outer catheter 62 is connected to a fixed part such as a clamp 131. The transport table 130 of the pullback system 63 includes a motor (not visible in FIG. 13) for driving the table in the direction indicated by arrow 132, thereby effecting longitudinal displacement of the inner catheter 62 (coupled to the connector which is coupled to the transport table 130) relative to the outer catheter 61 (which is coupled to the clamp 131). The controlled pullback operation driven by the motor during scanning is typically effected in the "withdrawing" or "pullback" direction indicated by the arrow 132. However it will be understood that the scan could also be performed by controlled longitudinal displacement in the "insertion" or "push" direction opposite to arrow 132 although care will have to be taken to ensure that the system cannot attempt to drive the distal end of the inner catheter 62 beyond the distal end of the outer catheter 61. Preferably, the motor can also return the inner catheter to a start position for a further pullback operation (e.g. for repeated scanning) although this function could also be performed by a manual latching reset function allowing temporary freedom of longitudinal movement of the inner catheter from the transport table 120, for example.

The pullback system 63 is applied to longitudinally displace the inner catheter 62 along the artery to acquire a 3D dataset. The pullback speed is preferably ≥100 mm per second. The pullback system 63 may include a linear motor. The stable rail or stator can be used as the fixed part (clamp 131) while the moving part can be used as the transport table 130.

The high-speed frequency-scanning laser 64 is a wavelength-scanning light source, e.g. with a centre wavelength of 1310 nm and a range of 1260-1360 nm. The scanning rate is preferably ≥200 kHz. In one preferred embodiment, a Fourier domain mode-locked laser can be used.

The interferometer 65 creates interference fringes of back-reflected light in two arms: the sample arm 15 and the reference arm 14. The sample arm 15 incorporates/connects to the fibre 72, 85 of the inner catheter 62 while the reference arm 14 provides the optical path that reflects from a mirror 10. the preferred embodiment of interferometer 65 in FIG. 6 is a fibre-based Michelson interferometer. Coherence fringes are generated in the second 2×2 coupler 17.

The data acquisition system 66 comprises a photodetector 18 and a digitizer 19. The photo detector converts the light signal (coherence fringes) into electronic signals. The digitizer 19 records the electronic signals. In the preferred embodiment of FIG. 6, the photodetector is a balanced detector to reduce noise levels. An image is constructed based on the data after inverse Fourier transform. The bandwidth of the digitizer 19 is preferably sufficient for acquisition of >800 samples per wavelength sweep of the laser.

Figure 14A:
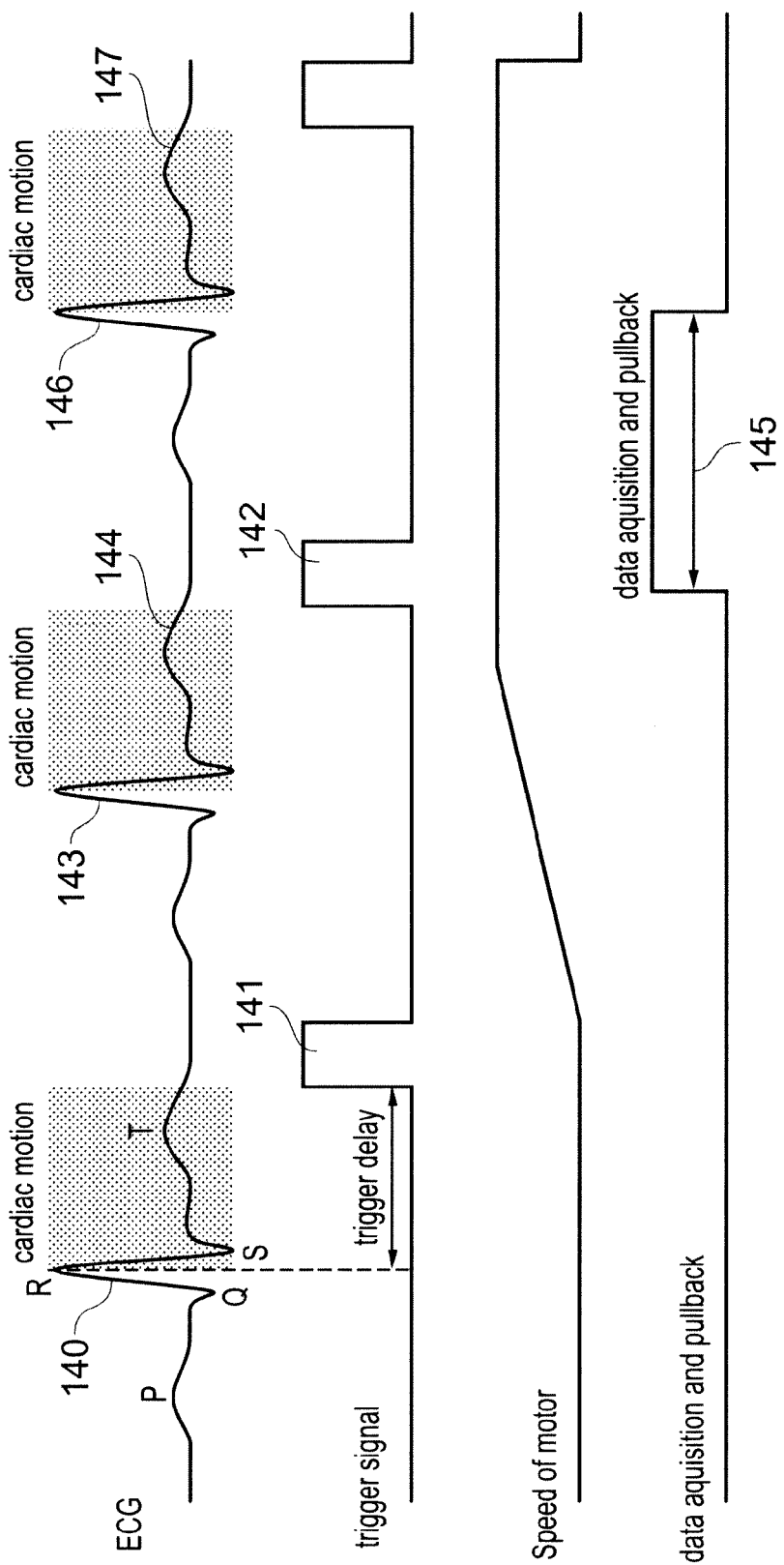
FIGS. 14a and 14b are time-aligned sets of graphs showing ECG triggering for pullback of the optical imaging system.

The ECG based trigger module 67 provides a system trigger signal for actuating the motor of the pullback system 63 and the data capture based on an ECG signal from the patient whose artery is being scanned. As now described with reference to FIG. 14a, in a preferred example, the positive slope of the QRS wave 140 can be used as an initial trigger for the system trigger signal 141, although other features (or combinations of features) of the ECG signal could be used. The features of the ECG signal to be used in any particular context could be adjustable or selectable by the user, e.g. to take into account particular distortions or measuring conditions for a specific patient. The initial system trigger signal 141 may be used to trigger the spin up of the optical element motor 81, and a subsequent trigger signal 142 may be used to initiate the pullback system operation and to effectuate the data acquisition.

Figure 14B:
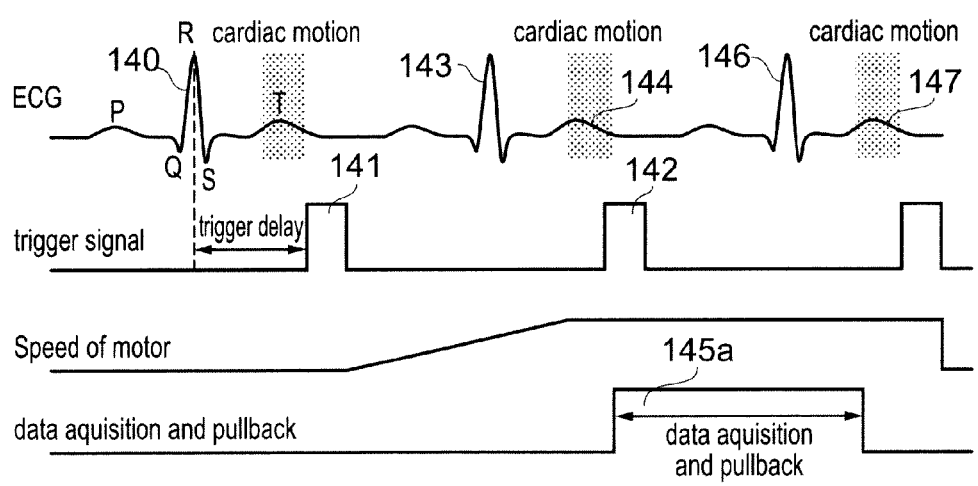

Although the system trigger signals 141, 142 may be generated by detection of the QRS wave 140 as a readily detectable ECG feature, the system trigger signal 142 for imaging is preferably delayed until the end of the T-wave 144 following the QRS wave 143. This is to avoid the period of strong cardiac motion. Preferably, the time period 145 between the T-wave 144 and the next R-wave 146 is used for imaging and pullback, which is typically 60-70% of the entire cardiac cycle. However, if the period of the QRS wave 143 is found not to result in excessive disturbance from cardiac motion then in some circumstances, as shown in FIG. 14b, the time period 145a for imaging could be extended to the beginning of the next T-wave 147.

The catheter micro-motor 81 needs a short period to accelerate to the target speed, which can be triggered by the first system trigger signal 141. After this trigger signal, one or several cardiac cycles can be used for the acceleration of the motor, thus the system trigger signal 142 used for initiating pullback and data acquisition need not be the immediately succeeding signal to initial trigger signal 141. After the motor 81 reaches the target speed, the data acquisition and pullback are triggered at the same time by the appropriate system trigger signal 142.

To suppress image artefacts caused by cardiac motion, it is necessary to finish imaging within the time period 145 extending from the end of the T-wave 144 to the next R-wave 146. It will be understood that imaging could be continued past this point if the significant data of interest have already been captured within this period.

In a general aspect, the trigger module 67 is operative to at least initiate an imaging scan based on cardiac event timing. That timing preferably involves the detection of a feature within the QRS complex and the assumption of a delay sufficient to pass the ensuing T-wave. However, any particular feature in the ECG data could be used if it provides sufficient temporal accuracy to initiate optical measurements within a period which is relatively undisrupted by cardiac motion. The trigger module may generally be operative not only to initiate an imaging scan, but also to stop the scan in time for a subsequent cardiac motion event.

A method of use of the intravascular optical imaging system 60 is as follows.

The imaging probe 70 comprising outer and inner catheters 61, 62 are inserted into the patient's artery, the inner catheter 61 being positioned at the start of the location of interest. The ECG trigger module 67 is coupled to the patient to obtain ECG data. The ECG-based trigger signal 141 may be used to switch on or speed up of the synchronous motor to the required rotational velocity. After sufficient (one or more) cardiac cycles to allow the required rotational velocity to be achieved and stabilised by the motor 81, an ECG-based trigger signal 142 is used to trigger the pullback system 63 and the data acquisition. With a pullback speed≥100 mm per second, the imaging of the relevant section of artery will be finished before the arrival of a subsequent R-wave 146.

Figure 15:
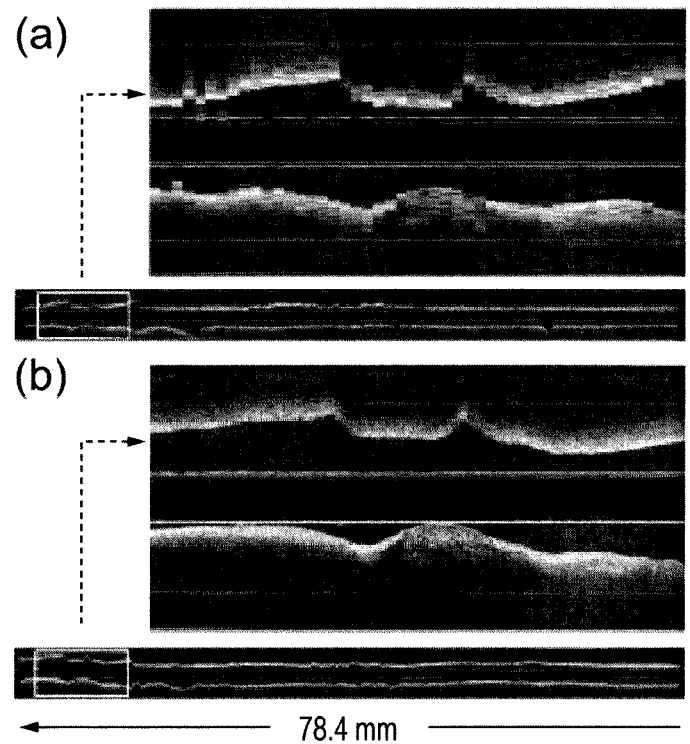
FIG. 15 is a set of OCT images acquired at two different rotational scan speeds but the same longitudinal pullback speeds.

The image can be constructed based on the inverse Fourier transform of the data. With higher laser wavelength sweep rate and catheters with higher circumferential scan speed, it is possible to decrease further the sampling interval along the artery and improve image quality. A catheter speed of 3200 rps used in combination with a 1.6 MHz sweep-rate laser has been demonstrated. The sample interval along the artery (i.e. the frame spacing) is decreased to 31 µm at a pullback speed of 100 mm per second. The image quality along longitudinal direction is improved as shown in FIG. 15. FIG. 15a shows an image derived from a dataset generated with an optical element rotating at 400 rps and a pullback rate of 100 mm/sec. By contrast, FIG. 15b shows an image derived from a dataset generated with an optical element rotating at 3200 rps and laser frequency 1.6 MHz and a pullback rate of 100 mm/sec.

Figure 16:
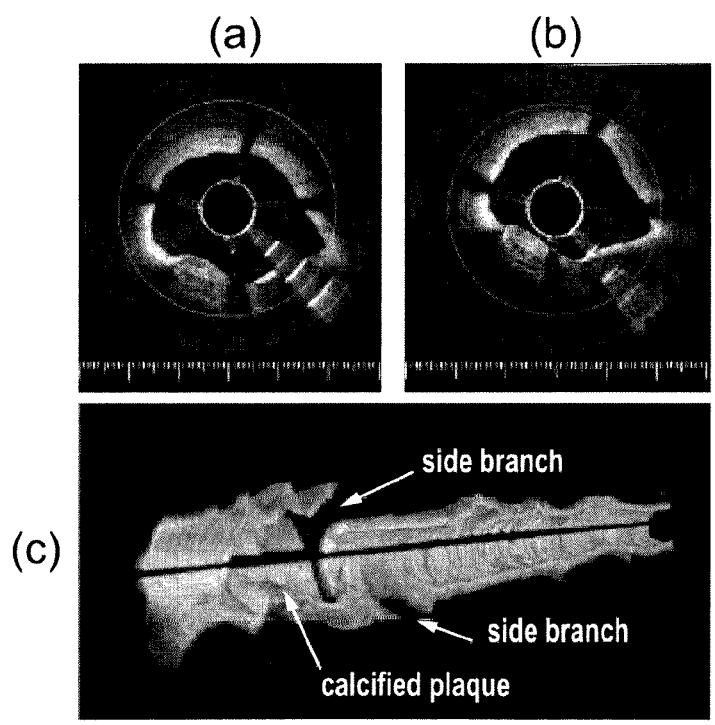
FIG. 16 is a set of images acquired by the OCT imaging system.

With a higher sweep rate and low scanning speed catheter, the image quality of 2D image can also be improved as shown in FIG. 16. In FIG. 16, the images are each acquired with 400 rps rotation speed and 1.6 MHz sweep rate of the laser. Each 2D image (FIGS. 16a and 16b) consists of 4000 lines. FIG. 16a shows a frame rate of 400 Hz (1000 lines averaged from 4000 lines) and FIG. 16b shows a frame rate of 3.2 kHz (500 lines). Averaging the lines in groups of four, resulting in 1000 image lines, gains a higher sensitivity.

The optical imaging system described herein is ideally suited for intracoronary imaging and can acquire a pullback data set of a relevant section of artery in a time less than one cardiac cycle. This approach to catheter-based coronary imaging eliminates the effects of cardiac motion on the dataset. Fast data acquisition can be achieved without sacrificing longitudinal sampling by a high-speed pullback system operating at >100 mm/s, a catheter or optical device rotation of >400 revolutions per second and a frequency-scanning laser system operating at >200,000 scans per second. A further advantage is a reduction of the flush volume required to create a blood-free field of view. Increasing the optical device rotation speed to >3200 rps allows the acquisition of an isotropically sampled dataset without motion artefacts. Although the preferred arrangement would be capable of acquiring a dataset for an entire length of artery in one pullback, it will be understood that only a relevant section of artery could be imaged, or the artery could be imaged in sections, e.g. overlapping sections. Each scan can be triggered to a cardiac event.

The imaging system described may generally be suitable for scanning any vessel walls in a context where pulsatile flow in the vessel or muscular activity near the vessel being imaged can cause disruption or disturbance to the measurement process and hence errors in datasets gathered therefrom, and where the timing of measurements can be suitably controlled by reference to cardiac events such as ECG waveforms to reduce the impact of the disruption or disturbance on the dataset. For example, the influence of the cardiac cycle can be seen in oesophageal scans.

As has been previously described, the trigger module 67 may generally be operative to only initiate an imaging scan if the duration of the scan is such that it can be completed within the expected time available. However, the trigger module 67 could also be configured to stop the scan in time for a subsequent cardiac motion event, and possibly even resume a scan during a next cardiac cycle. It would also be possible for the ECG-based trigger system 67 to more generally assess the duration of time period 145 available for scanning by monitoring a succession of cardiac cycles in the ECG data and then controlling one or more of the laser frequency scan rate; the frame rate (rotational speed) and the pullback speed to optimise use of an available measurement time period 145. Such optimisation could be used to achieve the best possible image quality for an available time period.

As described in connection with FIG. 8, the catheter-based imaging device can be mounted within or onto an inner catheter 62 which slides within and relative to an outer catheter 61. The inner catheter can be any structure configured to support the optical element 83, motor 81, fibre 85 and wires 84. The outer catheter can be any suitable structure for constraining the inner catheter within a vessel being imaged and suitable for the passage of optical radiation therethrough in a radial direction.

Although the embodiments described above with particular reference to FIGS. 6 and 14 use an ECG-based trigger, any mechanism for providing suitable cardiac event timing can be used to trigger the imaging scans. For example, cardiac event timing can be provided from various sensed or measured physiological signals from the patent. These physiological signals can include any one or more of ECG data; blood pressure measurement data (e.g. intracoronary or intracardiac pressure); blood oxygen measurement data; phonocardiogram data; and visual echocardiogram data. These can be acquired in real time using any one or more of one or more of: an ECG sensor; a blood pressure sensor, an SpO2 sensor; a phonocardiogram sensor; and a visual echocardiogram sensor. Thus, the ECG trigger module 67 can be replaced by, or supplemented with, any trigger module capable of initiating an imaging scan based on cardiac event timing data from any measurable physiological signals from the patient capable of providing cardiac event timing data.

Other embodiments are intentionally within the scope of the accompanying claims.

The invention claimed is:

1. A catheter-based optical imaging system for imaging a patient, comprising:
    a catheter-based imaging device configured to direct optical radiation towards a vessel wall and to receive reflected radiation therefrom;
    a displacement mechanism configured to vary the position of the imaging device relative to the catheter as a function of time during an imaging scan;
    an input configured to receive cardiac event timing data from the patient; and
    a trigger module configured to initiate an imaging scan based on the cardiac event timing data, wherein
        the imaging device comprises an optical element rotatable about the catheter longitudinal axis to generate frames of image data, each frame corresponding to at least part of a circumferential scan,
        the displacement mechanism comprises a longitudinal displacement mechanism configured to drive the optical element along a longitudinal axis of the catheter such that successive frames of image data correspond to different longitudinal positions, and
        the trigger module is configured to initiate longitudinal displacement of the optical element by the displacement mechanism by reference to a detected cardiac event, and is configured to complete a 3D imaging scan comprising the successive frames of the image data within one cardiac cycle defined between two cardiac events identified within the cardiac event timing data.

2. The imaging system of claim 1 in which the input module is configured to receive physiological signals from the patient, and the cardiac event timing data is obtained from the physiological signals.

3. The imaging system of claim 2 in which the cardiac event timing data is obtained from any one or more of: ecg data; blood pressure measurement data; blood oxygen measurement data; phonocardiogram data; and visual echocardiogram data.

4. The imaging system of claim 3 further including one or more of: an ecg sensor; a blood pressure sensor, an spo2 sensor; a phonocardiogram sensor; and a visual echocardiogram sensor.

5. The imaging system of claim 1 in which the trigger module is configured to stop the 3D imaging scan in time for a subsequent cardiac motion event.

6. The imaging system of claim 1 in which the trigger module is configured to effectuate the 3D imaging scan between the end of a cardiac t-wave and the beginning of a successive r-wave.

7. The imaging system of claim 1 in which the trigger module is configured to effectuate the 3D imaging scan between the end of a cardiac t-wave and the beginning of a successive t-wave.

8. The imaging system of claim 1 in which the trigger module is configured to effectuate the 3D imaging scan a predetermined time after detection of a selected cardiac event.

9. The imaging system of claim 1 in which the trigger module is further configured to initiate rotation of the optical element by reference to the detected cardiac event and to initiate said longitudinal displacement of the optical element in a period after initiating rotation, when the optical element has reached a predetermined speed of rotation.

10. The imaging system of claim 9 in which the detected cardiac event is one of a qrs complex or a t-wave.

11. The imaging system of claim 1 in which the detected cardiac event is one of a qrs complex or a t-wave.

12. The imaging system of claim 1 in which the optical element comprises a first transmissive interface, a second transmissive interface and a first reflective surface and in which the imaging system further includes a motor coupled to rotate the optical element.

13. The imaging system of claim 12 in which the first transmissive interface is positioned and configured to optically couple the optical element to an optical channel disposed along the catheter and the second transmissive interface is positioned and configured to direct optical radiation along optical paths extending radially from the catheter longitudinal axis, the first reflective surface being disposed between the first and second transmissive interfaces.

14. The imaging system of claim 13 in which at least one of the first transmissive interface, the second transmissive interface and the first reflective surface comprises a focusing element.

15. The imaging system of claim 1 further comprising an inner catheter slidably disposed within an outer catheter, in which the catheter-based imaging device is mounted to a distal end of the inner catheter, and in which the displacement mechanism comprises:
a motor-driven moveable part to which the proximal end of the inner catheter is attached; and
a fixed part to which the proximal end of the outer catheter is attached.

16. The imaging system of claim 1 in which the catheter-based imaging device is mounted to a distal end of an inner catheter, the inner catheter further comprising:
an optical conduit extending through the inner catheter from the proximal end to a position adjacent the imaging device for optical coupling thereto;
motor control cables extending through the inner catheter from the proximal end to a motor at the distal end of the inner catheter; and
a connector coupled to the proximal end of the inner catheter configured to communicate both optical conduit and motor control cables into the catheter.

17. A method of optical imaging within a vessel of a patient, comprising the steps of:
introducing a catheter-based imaging device into a vessel of a patient, the imaging device configured to direct optical radiation towards the vessel wall and to receive reflected radiation therefrom;
obtaining cardiac event timing data from the patient;
initiating an imaging scan based on the cardiac event timing;
rotating an optical element of the imaging device about the catheter longitudinal axis to generate frames of image data, each frame corresponding to at least part of a circumferential scan;
using a longitudinal displacement mechanism to vary the position of the imaging device relative to the catheter as a function of time during the imaging scan, the displacement mechanism driving the optical element along a longitudinal axis of the catheter such that successive frames of image data correspond to different longitudinal positions;
initiating longitudinal displacement of the optical element by the displacement mechanism by reference to a detected cardiac event; and
completing a 3D imaging scan comprising the successive frames of the image data within one cardiac cycle defined between two cardiac events identified within the cardiac event timing data.

18. The method of claim 17 in which the cardiac event timing data is derived from measured physiological signals from the patient.

19. The method of claim 17 in which the cardiac event timing data is obtained from any one or more of: ecg data; blood pressure measurement data; blood oxygen measurement data; phonocardiogram data; and visual echocardiogram data.

20. A catheter-based optical imaging system for imaging a patient, comprising:
an optical pathway extending along a catheter in an axial direction from a proximal end to a distal end;
an optical element disposed at the distal end of the catheter configured to direct optical radiation from the axial optical path to a radial optical path extending radially from the catheter longitudinal axis towards a vessel wall and to receive reflected radiation therefrom; wherein:
the optical element is rotatable about the catheter longitudinal axis so as to vary the direction of the radial optical path; and
the optical element comprises a first transmissive interface, a second transmissive interface and a first reflective interface.

21. The imaging system of claim 20 in which the first transmissive interface is positioned and configured to optically couple the optical element to the optical pathway extending along the catheter and the second transmissive interface is positioned and configured to direct optical radiation along the radial optical path, the first reflective surface being disposed between the first and second transmissive interfaces.

22. The imaging system of claim 21 in which at least one of the first transmissive interface, the second transmissive interface and the first reflective surface comprises a focusing element.

23. The imaging system of claim 22 in which the focusing element comprises a concave or convex surface or interface.

24. The imaging system of claim 23 in which the focussing element comprises a spherical surface.

* * * * *